United States Patent [19]

Tepic

[11] Patent Number: 4,808,184
[45] Date of Patent: Feb. 28, 1989

[54] METHOD AND APPARATUS FOR PREPARING A SELF-CURING TWO COMPONENT POWDER/LIQUID CEMENT

[75] Inventor: Slobodan Tepic, Davos, Switzerland

[73] Assignee: Laboratorium fur experimentelle Chirurgie Forschungsinstitut, Davos, Switzerland

[21] Appl. No.: 7,970

[22] PCT Filed: May 14, 1985

[86] PCT No.: PCT/EP85/00227

§ 371 Date: Jan. 12, 1987

§ 102(e) Date: Jan. 12, 1987

[87] PCT Pub. No.: WO86/06618

PCT Pub. Date: Nov. 20, 1986

[51] Int. Cl.[4] .............................. A61M 31/00
[52] U.S. Cl. .............................. 604/56; 604/87; 604/88; 623/16; 433/201.1; 222/82; 222/94; 215/DIG. 8
[58] Field of Search .............................. 206/219, 221; 215/DIG. 8; 222/82, 94, 196, 201, 256; 604/56, 87, 88, 203; 433/201.1; 623/16, 66

[56] References Cited

U.S. PATENT DOCUMENTS

| 1,718,597 | 6/1929 | Smith | 604/88 |
| 3,570,486 | 3/1971 | Engelsher | 604/88 |
| 3,951,387 | 4/1976 | Warden et al. | 206/219 |
| 4,239,113 | 12/1980 | Gross et al. | 206/568 |
| 4,463,875 | 8/1984 | Tepic | 604/87 |
| 4,467,588 | 8/1984 | Carveth | 604/87 |
| 4,516,967 | 5/1985 | Kopfer | 604/87 |
| 4,551,135 | 11/1985 | Gorman et al. | 623/16 |

FOREIGN PATENT DOCUMENTS

| 993588 | 7/1976 | Canada. |
| 2229702 | 12/1973 | Fed. Rep. of Germany. |
| 2801706 | 7/1979 | Fed. Rep. of Germany. |
| 1431211 | 6/1973 | United Kingdom. |

Primary Examiner—Richard J. Apley
Assistant Examiner—Paul Prebilic
Attorney, Agent, or Firm—Nutter, McClennen & Fish

[57] ABSTRACT

A method of preparing a self-curing two-component cement, which is particularly useful for the preparation of bone cement used in orthopedics, from a powder component and a liquid component. The method includes providing the powder component in a first at least partially evacuated inflexible container, providing the liquid component in a second inflexible container, and adding the liquid component to the evacuated powder component, such that the liquid floods the evacuated interspaces between the powder particles. An apparatus for carrying out this process is a syringe with a slidable piston, the syringe being sealed at its dispensing end by a removable plug. Preferably, the syringe is fitted with an axially collapsible spiral mixing device, one end of which is an elongated shaft which extends through the removable plug at the dispensing end. The elongated shaft can be rotated to homogenize the contents of the syringe, but during dispensing the mixing device collapses as the piston advances.

14 Claims, 8 Drawing Sheets

METHOD AND APPARATUS FOR PREPARING A SELF-CURING TWO COMPONENT POWDER/LIQUID CEMENT

This invention relates to a method and apparatus for preparing a cement composed of a powder and a liquid component which polymerize when brought into contact with each other. The invention is especially useful in connection with a cement which is used for medical purpose, particularly as bone cement or denture base material.

BACKGROUND OF THE INVENTION

Many modern day bone cements of the two component powder/liquid type are known which, when thoroughly mixed together, undergo polymerization thereby forming a hard and more or less durable cement mass.

While the present invention can be used to prepare a variety of such cements, it is especially useful in the preparation of so-called bone cement used to anchor and support artificial joint components and other prostheses in natural bone. Accordingly, it will be described here specifically in that context.

The currently preferred bone cement is polymethylmethacrylate or so-called PMMA. PMMA is comprised of a powdered polymer and a liquid monomer. Upon mixing, these components polymerize within minutes so as to form a firm rigid bond between the prosthesis and the surrounding bone structure in which the prosthesis is placed.

The present procedure for preparing PMMA bone cement is to thoroughly mix the powder and liquid component in order to start polymerization whereby the cement mass turns to a putty or dough consistency. The partially cured cement is then applied to the bone structure to be treated, e.g. into the medullary canal of the femur which is receiving a femoral shaft of a hip joint prosthesis.

All known methods for mixing bone cement have serious drawbacks, the most essential being:
  poor mixing, which depends on the individual mixing technique;
  high exotherm, due to the considerable amount of liquid component necessary to produce an applicable cement mass by conventional mixing techniques;
  creation of porosities by inclusion and entrapment of air bubbles as well as by evaporation of excess monomer resulting in significant degradation of the mechanical properties of the cured cement.

SUMMARY OF THE INVENTION

Accordingly, the present invention aims to provide an improved method and apparatus for preparing a two component cement which is independent from the individual mixing technique.

Another object of the invention is to provide such a method which by its reduced amount of liquid component necessary to produce an applicable cement mass lowers considerably the maximum temperature reached during polymerization.

Still another object of the invention is to provide such a method which eliminates porosities in the cured cement by exclusion of air and by prevention of monomer evaporation.

DETAILED DESCRIPTION OF THE INVENTION

Figure 1:
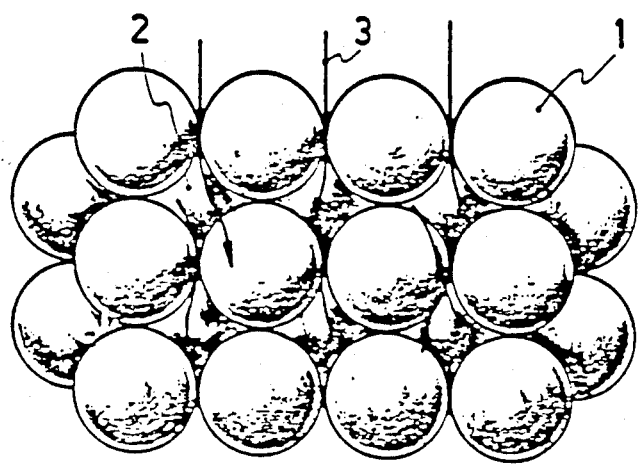
FIG. 1 is a perspective view of the powder component particles in a tightly packed state as used for the invention.

As illustrated in FIG. 1 the powdered component of the cement 1 is packed as tightly as possible in the container 4 (FIG. 2) and the container is evacuated. Thus void space 2 contains no, or very little air. When allowed to enter the container 4, the liquid component will flood (arrow 3) void space 2 between the powder particles. This is the initial phase of the mixing process producing a powder-liquid mixture without any, or with very little air inclusion.

Figure 2:
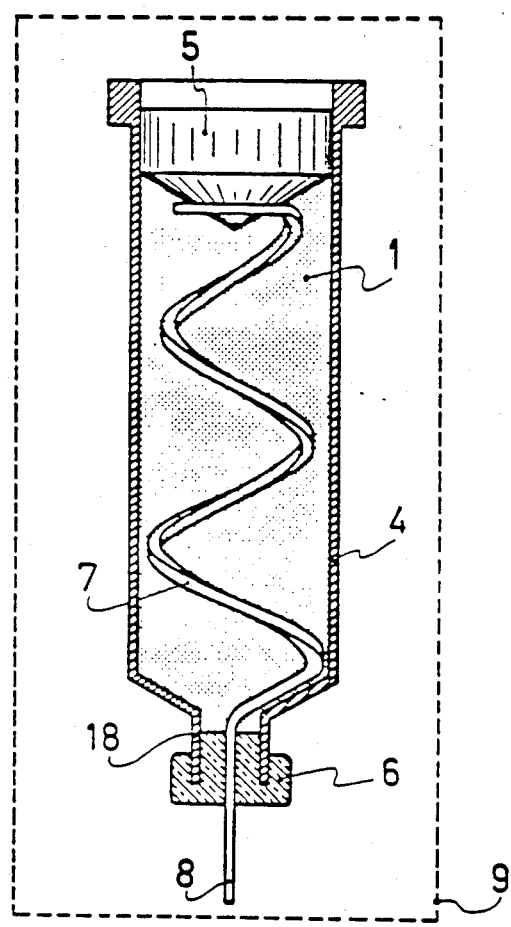
FIG. 2 is a sectional view of the syringe type container for the powder component used in the apparatus according to the invention.

FIG. 2 shows a pre-packaged powder component 1 in the container 4. Container 4 is of a syringe type with piston 5. The extrusion end 18 of the container is closed with a plug 6. An internal mixing device 7 protrudes through the plug 6 with its shaft 8. The container is evacuated in the packaging process. For increased shelf life the outer package 9 is also evacuated and sealed. It may be made of aluminum foil for example. It may also serve as the sterile outer package.

Figure 3:
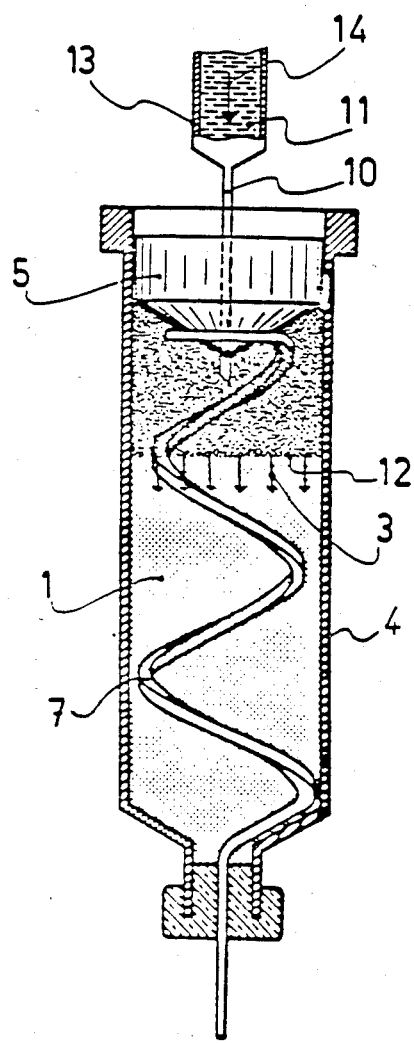
FIG. 3 shows the liquid component injection through the piston of the syringe type container in a sectional view.
Figure 7:
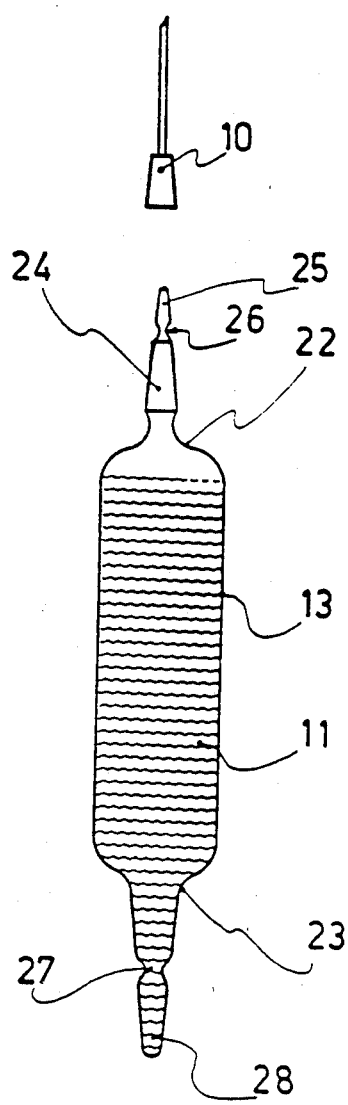
FIG. 7 is a sectional view of the ampule used for the invention.

FIG. 3 shows the liquid component injection. This is done prior to application upon removal of the container 4 from the package 9. A needle 10 is inserted through the elastomer part of piston 5. Liquid component of the cement, which predominantly consists of methylmethacrylate 11 enters the container 4 and floods as indicated by arrows 3 the powder component particles 1. Flooding front 12 advances as described in more detail later (reference is made to FIG. 8 description). Liquid component 11 may be ejected as indicated by arrow 14 from its container 13 either by a piston if 13 is a syringe, or simply sucked out by the vacuum in the container 4 if the container 13 is an ampule as shown in FIG. 7.

Figure 4:
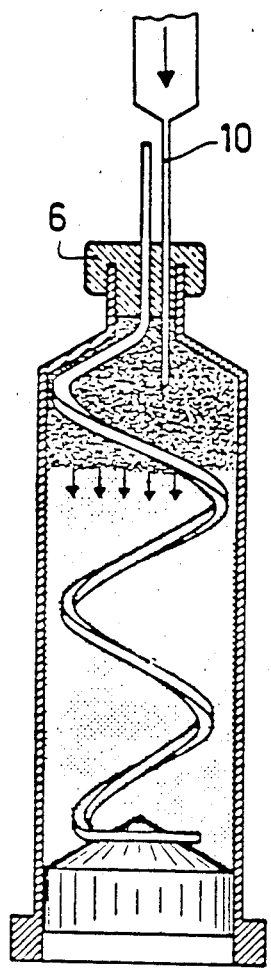
FIG. 4 shows the liquid component injection through the plug of the syringe type container in a sectional view.

FIG. 4 shows the liquid injection through the plug 6 with the air of the needle 10.

Figure 5:
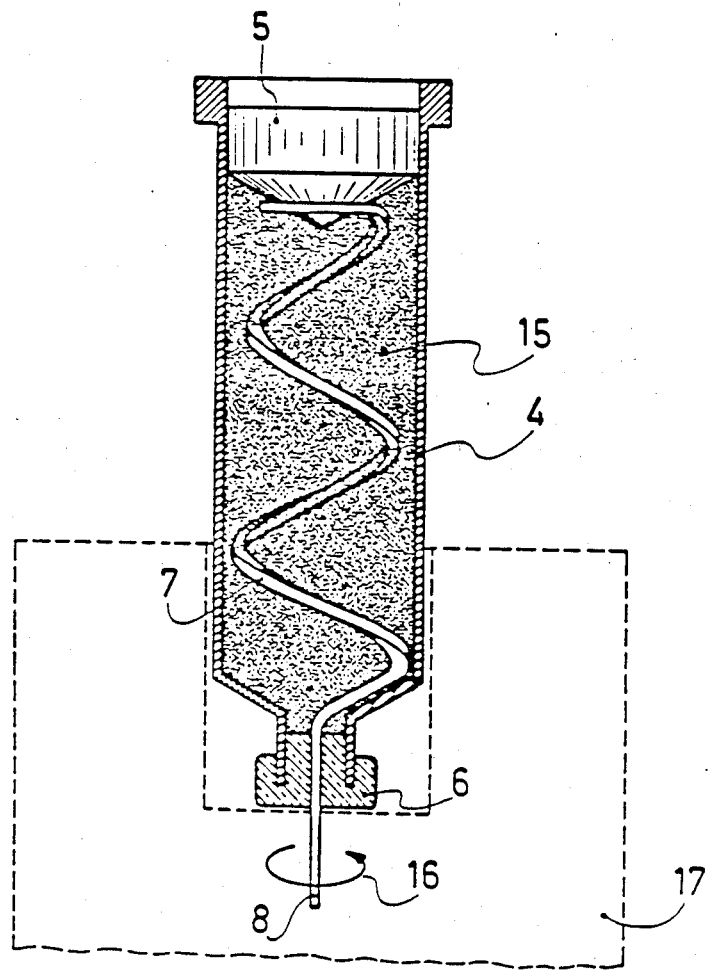
FIG. 5 is a sectional view of the syringe type container showing the internal mixing process step.

FIG. 5 shows additional homogenization of the mixture 15 by means of the internal mixing device 7. Since flooding alone may not produce a mixture uniform enough for the critical medical applications such as bone cement, means for additional mechanical mixing is provided in that an axially collapsible mixing device 7 is enclosed and sealed within the container 4. It may be made of a suitable metal, or plastic.

Its shaft 8 protrudes through the plug 6 which ensures air tight seal of the container 4. The shaft 8 may be gripped in the chuck of say a power drill and turned as indicated by arrow 16. It may also be inserted in the specially provided mixer 17. The end of the shaft 8 may be adapted for simple coupling to the mixer 17. Time allowed for homogenization depends on the rate of the polymerization and is typically a few minutes. Since handling of the cement is minimized and no settling time is needed for air bubbles to come out of the mixture as it is the case in the conventional mixing, a major advantage of this procedure arises—mixing time may be increased many-fold. There is no monomer evaporation since the container 4 remains sealed throughout the injection and homogenization phases.

Figure 6:
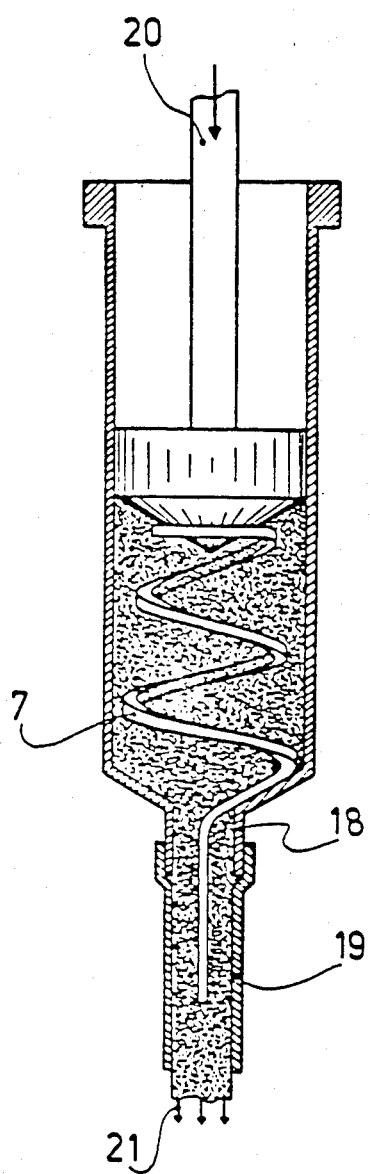
FIG. 6 is a sectional view of the syringe type container with an additional nozzle showing the extrusion process step.

FIG. 6 shows extrusion 21 of the cement following homogenization. For that a piston rod 20 is pushed in following removal of the plug 6. Extrusion may be done through the container end 18 or through an additional nozzle 19 attached to the container end 18.

FIG. 7 shows a preferred embodiment of the liquid component container 13. It is in the form of a glass ampule. Narrowed end 22 is shaped so as to allow needle attachment onto the conus 24. The cap 25 is broken-off at the neck 26. The needle 10 is attached to the conus 24. The ampule is then turned upside-down and the needle 10 is inserted into the container 4 through either the piston 5 or the plug 6. The cap 28 on the other narrowed end 23 of the ampule 13 is then broken-off at the neck 27 allowing the liquid 11 to flood the powder component particles 1 in the container 4 as shown in FIGS. 3 and 4.

Figure 8:
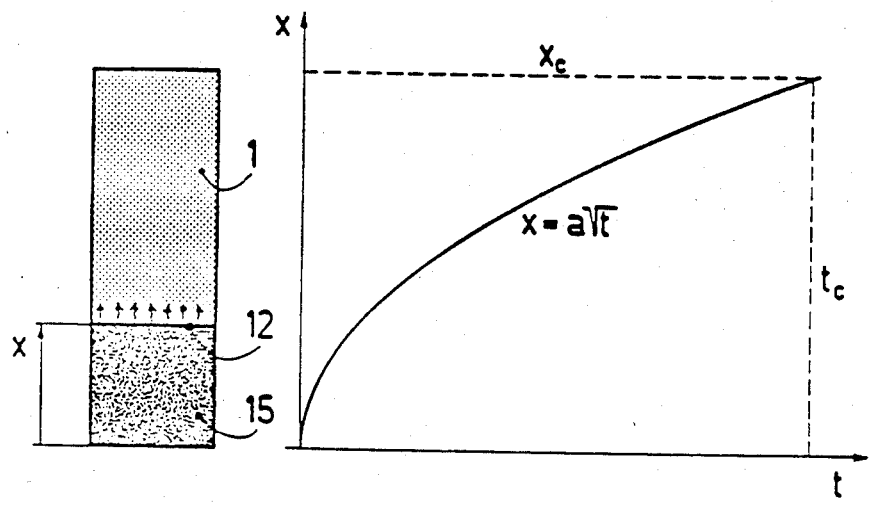
FIG. 8 is a diagram showing the dynamics of the flooding process of the invention.

FIG. 8 shows the dynamics of the flooding process, wherein pressure drop in the injection needle 10 is neglected. Flooding front 12 position x in the powder column 1 is proportional of the square root ot time. The constant of proportionality a depends on the powder column permeability, the liquid viscosity and the column cross-section. The front 12 will arrive at the end of the column $x_c$ in finite time $t_c$ and with finite speed.

In the process of the present invention, preferably the weight ratio of the powder component to the liquid component is between 2.4 and 3.6, and more preferably between 3.0 and 3.6. The particles of the powder component are preferably approximately uniform in size and of generally spherical form. In a preferred embodiment, the majority of powder particles have diameters in the range of 10 to 100 $\mu$m. In a further preferred embodiment, the evacuated interspaces between the powder particles comprise 25 to 35 percent, more preferably 26 to 30 percent, of the total volume of the powder.

In another preferred embodiment, the particles of the powder component are coated with a polymerization catalyst, preferably a peroxide. The cement mixture of the present invention can also comprise additional components, such as radio-opaquers or antibiotics. Preferably these additional components are provided in a form geometrically similar to the particles of the powder component.

I claim:

1. A method of preparing a self-curing cement from a powder component containing a polymerization catalyst and a liquid component containing a polymerizable monomer, comonomer, prepolymer or mixtures thereof, said method comprising:
   A. supplying said powder component in an at least partially evacuated, sealed chamber of a first inflexible container, said powder component comprising particles of said powder and interspaces therebetween;
   B. supplying said liquid component in a second inflexible container;
   C. connecting said second container to said first container by means of an air-tight connection;
   D. pressurizing said liquid component to a pressure higher than that of said partially evacuated chamber; and
   E. propelling said liquid component into said partially evacuated container, whereby said liquid floods said partially evacuated interspaces by the action of the pressure difference between the pressure on the liquid component and the pressure in the interspaces, thereby forming a polymerizable cement mass.

2. The method of claim 1 wherein said first container comprises a syringe, said syringe comprising:
   A. a barrel which is open at its rearward end and which includes a dispensing outlet at its forward end;
   B. piston means reciprocably mounted in said barrel and defining a sealed chamber forward thereof for containing said powder component;
   C. closure means removably mounted on said forward end of the barrel; and
   D. an elastomeric injection port into said chamber, wherein said connecting, pressurizing and propelling steps comprise injecting said liquid component into said chamber by means of a hollow needle inserted through said elastomeric port.

3. The method of claim 15 further comprising mechanically mixing said polymerizable cement mass, said mechanical mixing step comprising:
   providing said syringe with an axially collapsible, rotatable, spiral mixing member disposed in said chamber with one end of said spiral member being elongated and extending through said closure means; and
   rotating said elongated end of said mixing member, thereby rotating the spiral portion of said mixing member disposed in said chamber.

4. The method of claim 3 further comprising dispensing said polymerizable cement mass, said dispensing step comprising:
   removing said closure means from said syringe while leaving said collapsible spiral mixing member in place; and
   advancing said piston means to force said polymerizable cement mass out of said chamber through said dispensing outlet.

5. The method of claim 14 wherein said pressurizing comprises opening said second inflexible container to atmospheric pressure, and wherein said propelling is effected by the force of said atmospheric pressure.

6. The method of claim 1 wherein the weight ratio of said powder component to said liquid component is in the range between 2.4 and 3.6.

7. The method of claim 6 wherein said weight ratio range is between 3.0 and 3.6.

8. The method of claim 1 wherein said particles of said powder component are of approximately uniform size and approximately spherical form.

9. The method of claim 1 wherein the majority of said particles of said powder component have a diameter in the range of 10 to 100 microns.

10. The method of claim 1 wherein the volume of said interspaces comprises 25 to 35 percent of the total volume of said powder component.

11. The method of claim 10 wherein the volume of said interspaces comprises 26 to 30 percent to the total volume of said powder component.

12. The method of claim 1 wherein said powder particles are coated with a polymerization catalyst.

13. The method of claim 12 wherein said polymerization catalyst is a peroxide.

14. The method of claim 1 wherein said powder component further comprises radio-opaquers or antibiotics in a particulate form similar to that of said powder particles.

* * * * *